(12) United States Patent
Galibert et al.

(10) Patent No.: US 10,480,010 B2
(45) Date of Patent: Nov. 19, 2019

(54) BACULOVIRUS EXPRESSION SYSTEMS

(75) Inventors: Lionel Galibert, Levallois-Perret (FR); Otto-Wilhelm Merten, Crespiéres (FR); Monique Van Oers, Renkum (NL); Christel Riviere, Boutigny-sur-Essonne (FR)

(73) Assignee: GENETHON, Evry (FR)

( * ) Notice: Subject to any disclaimer, the term of this patent is extended or adjusted under 35 U.S.C. 154(b) by 0 days.

(21) Appl. No.: 14/234,949

(22) PCT Filed: Jul. 27, 2012

(86) PCT No.: PCT/EP2012/064843
§ 371 (c)(1),
(2), (4) Date: Jul. 21, 2014

(87) PCT Pub. No.: WO2013/014294
PCT Pub. Date: Jan. 31, 2013

(65) Prior Publication Data
US 2014/0356904 A1  Dec. 4, 2014

Related U.S. Application Data

(60) Provisional application No. 61/512,142, filed on Jul. 27, 2011.

(51) Int. Cl.
*C12N 15/86* (2006.01)

(52) U.S. Cl.
CPC .... *C12N 15/86* (2013.01); *C12N 2710/14033* (2013.01); *C12N 2710/14052* (2013.01); *C12N 2710/14144* (2013.01); *C12N 2750/14143* (2013.01)

(58) Field of Classification Search
None
See application file for complete search history.

(56) References Cited

U.S. PATENT DOCUMENTS 5,571,709 A * 11/1996 Devauchelle .......... C12N 15/86
435/235.1

OTHER PUBLICATIONS

Gailbert et al., Advanced Symposium and EMBO Practical Course on Viral Vectors in Gene Therapy: Applications & Novel Production Methods, Kuopio, Finland, Aug. 25-Sep. 4, 2010.*
Smith et al., Molecular Therapy, 2009, vol. 17, pp. 1888-1896.*
Baculovirus Expresssion Vector System, 6th Edition, May 1999, Pharmingen, 118 total pages.*
Berger et al., Multibac Expression System, 2004, 18 pages total.*
Kuzio et al., Virology, 1989, vol. 173, issue 2, pp. 759-763.*
Sokolenko et al., "Getting More from Cell Size Distributions: Establishing More Accurate Biovolumes by Estimating Viable Cell Populations" 2696) Biotechnology Progress 1787-1795 (Sep. 23, 2010).*
Vannuci et al., "Viral vectors: a look back and ahead on gene transfer technology" 36 New Microbiologica 1-22 (2013).*
R. B. Hitchman et al, "Genetic Modification of a Baculovirus Vector for Increased Expression in Insect Cells." Cell Biol. Toxicol., vol. 26, pp. 57-68, 2010.
R. B. Hitchman et al., "Improved Expression of Secreted and Membrane-Targeted Proteins in Insect Cells." Biotechnol. Appl. Biochem., vol. 56, pp. 85-93, 2010.
S. A. Kaba et al., "Development of a Chitinase and V-Cathepsin Negative Bacmid for Improved Integrity of Secreted Recombinant Proteins." Journal of Virological Methods, vol. 122, pp. 113-118, 2004.
R. H. Smith et al., "A Simplified Baculovirus-AAV Expression Vector System Coupled with One-Step Affinity Purification Yields High-Titer rAAV Stocks from Insect Cells." Molecular Therapy, vol. 17, No. 11, pp. 1888-1896, Nov. 2009.
L. Galibert et al., "Latest Developments in the Large-Scale Production of Adeno-Associated Virus Vectors in Insect Cells Toward the Treatment of Neuromuscular Diseases." Journal of Invertebrate Pathology, vol. 107, pp. S80-S93, 2011.
H. Chaabihi et al., "Competition Between Baculovirus Polyhedrin and p10 Gene Expression During Infection of Insect Cells." Journal of Virology, vol. 67, No. 5, pp. 2664-2671, May 1993.
R. B. Hitchman et al., "Optimizing the Baculovirus Expression Vector System." Methods, vol. 55, pp. 52-57, 2011.
L. Gailbert et al., "Baculovirus Deleted for Chitinase, Cathepsin and p10 Genes Improves Purified rAAV8 Quality." Wageningen UR Publication, 2006. (Abstract).
Galibert, L. "Baculovirus deleted for chitinase, cathepsin and p10 genes improves purified rAAv8 quality", Agenda for Symposium and EMBO Practical Course: Viral Vectors in Gene Therapy: Applications & Novel Production Methods, A. I. Virtanen Institute, University of Eastern Finland, Kuopio, Finland, Aug. 26-Sep. 4, 2010, obtained from internet: http://clinigene.plugis.com/assets/files/pdf/Educational/Program_Kuopio.pdf, pp. 1-10.
Brochure for Advanced Symposium and EMBO Practical Course: Viral Vectors in Gene Therapy: Applications & Novel Production Methods, A. I. Virtanen Institute, University of Eastern Finland, Kuopio, Finland, Aug. 26-Sep. 4, 2010, obtained from internet: http://www.vinnova.se/upload/dokument/EU_o_Internationellt/Broschyrer_rapporter/EMBO%20Eurolab.pdf, pp. 1-2.

* cited by examiner

*Primary Examiner* — Nancy J Leith
(74) *Attorney, Agent, or Firm* — Saliwanchik, Lloyd & Eisenschenk

(57) ABSTRACT

The present invention relates to an optimized baculovirus construct useful for the production of virus(-like) particles or viral vectors, in particular viral vectors for gene therapy.

9 Claims, 5 Drawing Sheets
Specification includes a Sequence Listing.

BACULOVIRUS EXPRESSION SYSTEMS

The present invention relates to an optimized baculovirus construct useful for the production of virus(-like) particles or viral vectors, in particular viral vectors for gene therapy.

BACKGROUND OF THE INVENTION

The baculovirus expression vector system (BEV) is used to produce high levels of recombinant proteins in insect cells. It is generally based on the deletion of the baculovirus polyhedrin gene (polh), which is replaced by the gene to be expressed under the control of the polh promoter. Incorporation of a bacterial origin of replication, an antibiotic resistance gene and an acceptor Tn7 recombination site into the baculovirus genome (i.e.: bacmid) has greatly improved this system, making it much faster to generate recombinant viruses (Luckow et al., 1993). Most commercially available baculovirus vectors lack the polh gene and otherwise have a complete genome, although Oxford ExpressionbTechnologies company distribute, with flashBACGOLD, a baculovirus vector negative for chitinase and cathepsin genes. It was thus anticipated that this expression system could be improved. Deletion of the chitinase and cathepsin genes from the AcMNPV genome has been shown to have a positive effect on intracellular and secreted recombinant protein stability (Kaba et al., 2004). It has also been shown that a BEV deficient in chitinase, cathepsin, p26, p10 and p74 allowed production of higher levels of recombinant proteins than those obtained with non-deletion viruses (Hitchman et al., 2009). However, expression data obtained in this latter study concerned only single recombinant proteins. For the production of complex structures such as viral vectors and virus-like particles, it is necessary to produce one or a number of proteins and, in the case of viral vectors, also a viral genome. From the results of Hitchman et al., it was not evident that the production of such complex structures could be improved in terms of protein quality when the chitinase, cathepsin, p26, p10 and p74 genes are deleted.

The aim of the present study was to provide an optimized baculovirus expression system for the production of virus vectors and/or virus-like particles.

DESCRIPTION OF THE INVENTION

An aspect of the present invention relates to a recombinant baculovirus genome comprising the p26 and p74 baculoviral gene ORFs, while the baculoviral genes cathepsin, chitinase and p10 are disrupted. In one preferable embodiment, the p10 gene is disrupted without deleting the p10 promoter. In another embodiment, the recombinant baculovirus genome comprises one or more heterologous sequence(s) of interest.

Another aspect of the invention relates to a recombinant baculovirus genome, wherein the baculoviral genes cathepsin, chitinase, p26, p74 and p10 are disrupted, and wherein the recombinant baculovirus genome comprises a heterologous sequence coding a part of a viral vector or virus-like particle.

In a further aspect, the invention provides a recombinant baculovirus comprising a recombinant baculovirus genome as described above.

In another aspect the invention provides a method for producing a recombinant baculovirus, comprising culturing a prokaryotic cell containing the recombinant baculovirus genome of the invention under conditions allowing production of a baculovirus.

In another aspect, a host cell comprising a recombinant baculovirus genome of the invention is provided.

A further aspect provides a method for producing a recombinant protein or nucleic acid (e.g. an RNA or DNA molecule or a recombinant genome—the recombinant genome being for example a RNA or DNA genome), comprising the step of culturing a host cell with one or several recombinant baculovirus(es) of the invention, wherein the heterologous sequence of interest encodes a recombinant protein or nucleic acid.

In another aspect, the invention provides a method for producing a viral vector or virus-like particle, comprising the step of culturing host cells with one or several recombinant baculoviruses each comprising a recombinant baculovirus genome harboring a heterologous sequence of interest useful for producing said viral vector or virus-like particle, wherein all recombinant baculoviruses comprise a recombinant baculoviral genome with intact p26 and p74 baculoviral gene ORFs, and wherein the baculoviral gene ORFs for cathepsin, chitinase and p10 are disrupted, and wherein the p10 gene promoter is not disrupted.

In another aspect, the invention provides a method for producing a viral vector or virus-like particle, comprising the step of culturing a host cell with one or several recombinant baculoviruses each comprising a recombinant baculovirus genome harboring a heterologous sequence of interest useful for producing said viral vector or virus-like particle, wherein all recombinant baculoviruses comprise a recombinant baculovirus genome wherein the baculoviral genes cathepsin, chitinase, p26, p74 and p10 are disrupted.

In one embodiment, the above methods are implemented for the production of a recombinant AAV vector.

The present invention relates to optimized recombinant baculovirus genome and methods using the same. It was surprisingly found that disruption of cathepsin, chitinase and p10 genes did not improve the level of recombinant AAV (rAAV) particles produced in insect cells, but allowed the production of rAAV particles with improved infectivity for mammalian cells. This result was highly unexpected as Hitchman et al. (cf. supra) reported higher expression levels of individual recombinant proteins produced from cathepsin-, chitinase-, p26-, p10- and p74-null baculovirus, although this study did not report production of a viral vector. The results presented here show in particular that the expression level of the AAV cap gene, encoding VP1, VP2 and VP3, is not improved with a baculovirus where the above mentioned baculovirus genes are disrupted (which results differs from what would have been expected from the disclosure of Hitchman et al.). Instead the level of degradation of VP1 and VP2 is reduced and the rAAV particles produced with this deletion baculovirus show a four-fold improvement in infectivity when compared to rAAV particles produced from a wild type baculovirus production system bacmid, i.e., not modified for chitinase, cathepsin, p26, p10, and/or p74 loci.

The recombinant baculovirus genome of the invention is preferentially capable of replication in an insect cell and in a prokaryotic cell such as *E. coli*. In particular, any viral baculovirus genome that contains a BAC replicon may be used. In a particular embodiment, the recombinant baculovirus genome is a bacmid. Suitable baculovirus sequences include the *Autographa californica* (Ac) MNPV bacmid.

Baculoviruses are commonly used for the infection of insect cells for the expression of recombinant proteins. In particular, expression of heterologous genes in insects can be accomplished as described in for instance U.S. Pat. No. 4,745,051; Friesen et al., 1986; EP 127,839; EP 155,476;

Vlak et al., 1988; Miller et al., 1988; Carbonell et al., 1988; Maeda et al., 1985; Lebacq-Verheyden et al., 1988; Smith et al., 1985; Miyajima et al., 1987; and Martin et al., 1988. Numerous baculovirus strains and variants and corresponding permissive insect host cells that can be used for protein production are described in Luckow et al., 1988, Miller et al., 1986; Maeda et al., 1985, McKenna, 1989, van Oers, 2011, and Lynn, 2007.

According to the present invention, any baculovirus genome derived from a baculovirus commonly used for the recombinant expression of proteins and biopharmaceutical products may be used. For example, the baculovirus genome may be derived from for instance AcMNPV, *Bombyx mori* (Bm)NPV, *Helicoverpa armigera* (Hear) NPV) or *Spodoptera exigua* (Se) MNPV, preferably from AcMNPV. In particular, the baculovirus genome may be derived from the AcMNPV clone C6 (genomic sequence: Genbank accession no. NC_001623.1) or E2 (Smith & Summers, 1979).

The invention implements the disruption of baculovirus genes. Several strategies may be implemented for this purpose, and in particular the mutation, for example by deletion, of the selected gene(s) from the (recombinant) baculovirus genome. A well known and established method to investigate gene functions is the manipulation of a baculovirus genome in bacteria by homologous recombination using ET (*E. coli*. RecE & RecT proteins) or lambda red based recombination directed at a single gene or a stretch of flanking genes, which is then replaced by an antibiotic selection marker (Datsenko & Wanner, 2000; Westerberg et al., 2010). In order to prepare multiple deletions within the same genome, several different selection markers need to be used or the selection marker needs to be flanked by unique restriction sites, allowing removal after each gene deletion, by digestion and re-ligation. A strategy derived from a method to make sequential deletions/insertions in a bacterial genome (Suzuki et al., 2007; Suzuki et al., 2005) has been adapted for bacmid technology (Marek et al., 2011) and has been used efficiently in the present study. It implements a modified cre-lox recombinase system that uses modified loxP sites to make serial mutations. After replacement of the first gene with a selection marker, for example the chloramphenicol acetyl transferase antibiotic marker, by homologous recombination, the marker can be removed due to the presence of loxP sites at both ends of the marker. In the setup used, two modified loxP sites are used (lox66 and lox71), each with a different mutation. After recombination by cre-recombinase a lox72 site is left (Lambert et al., 2007), which has now two mutations instead of one, and can no longer be recognized by the cre-recombinase. This allows the subsequent deletion of a second target gene.

In a particular embodiment, the chi/v-cath (nucleotides 105282-107954 according to AcMNPV genetic map (Ayres et al., 1994) and p10 (nucleotides 118839-119121) genes are disrupted.

In a particular embodiment, the disruption of the p10 gene is made concomitantly with the disruption of all or a part of the coding sequence of the p26 and/or p74 genes, preferably p26 and p74 genes (nucleotides 118044-121072).

In another particular embodiment, the disruption of p10 is made without disrupting the adjacent p26 and p74 gene ORFs. In one preferable variant of this embodiment, the recombinant baculovirus genome of the invention still comprises the p10 promoter (the p10 coding sequence is thus disrupted without deleting its promoter, which correspond to nucleotides 118739-118836 according to AcMNPV genetic map). In another embodiment, the p10 promoter is also deleted. It is shown below that the disruption of p10 gene ORF while leaving its promoter intact and without disrupting p26 and p74 gene ORFs allows the production of more effective rAAV viral particles than when these three genes are disrupted in the recombinant baculovirus genome.

The present recombinant baculovirus genome can be used to produce recombinant proteins or nucleic acids according to methods well known in the field of baculovirus-based expression systems. The recombinant baculovirus genome can thus also harbor heterologous nucleotide sequences useful for the production of recombinant proteins, nucleic acids or for the production of complex structures such as virus vectors and virus-like particles.

According to the invention, a heterologous nucleotide sequence is a sequence useful for the production of a product of interest (e.g. a protein, a nucleic acid such as a mRNA, siRNA, antisense nucleotide sequence, hairpin sequence, a virus genome such as a recombinant virus genome for gene therapy).

As such, the present invention also relates to a recombinant baculovirus genome (and recombinant baculovirus and host cells comprising the same) as defined above, comprising a heterologous sequence.

The heterologous sequence can be inserted in a site or locus known in the baculovirus to allow the expression of the inserted sequence. For example, the polyhedrin locus is classically used as an insertion site for heterologous nucleotide sequences (in particular via the Tn7 recombination site of the bacmid).

The invention also relates to a recombinant baculovirus and a host cell comprising the recombinant baculovirus genome of the invention.

The recombinant baculovirus of the invention is well-adapted to produce complex structures such as virus vectors or virus-like particles. In the latter case, the components of the complex structure can be expressed from several recombinant baculovirus genomes, each of said genomes carrying at least one component of the complex structure, and each of said components being encoded by heterologous nucleotide sequences comprised in different recombinant baculoviruses of the invention. When such a set of recombinant baculoviruses is used to produce several recombinant components, preferably all baculovirus vectors should have the same modifications in the chitinase, cathepsin, p26, p74, and p10 genes.

For example, for the production of a recombinant AAV, a system comprising three baculoviruses can be used: a baculovirus encoding the AAV Rep proteins, a baculovirus coding the AAV Cap proteins and a baculovirus coding the AAV-ITR genome comprising a gene of interest (e.g. a therapeutic gene) between the two AAV ITRs (Manno et al., 2006; Mendell et al., 2010; Simonelli et al., 2010). A system comprising two baculoviruses (dual-infection system) is also available now, for which the DNA sequences coding for the AAV Rep proteins and the AAV Cap proteins are provided by one baculovirus. The latter dual-infection system is implemented in the examples.

As such, the present invention also relates to a recombinant baculovirus genome (and recombinant baculovirus and host cells comprising the same) as defined above, comprising a heterologous sequence coding a part of a viral vector or of a virus-like particle. In a particular embodiment, the baculovirus vector encodes:

a rAAV genome, or
AAV Rep proteins, or
AAV Cap proteins, or
AAV Assembly Activating Protein (AAP).

In a particular embodiment, the recombinant baculovirus genome comprises an expression cassette comprising the AAV rep and cap genes, preferably in inverse orientation.

The host cell can be a producer cell for the production of a recombinant protein, nucleic acid, virus or virus-like particle, which has been infected by one or more baculoviruses according to the invention. Of course, the promoter(s) and the 5' and 3' untranslated regions such as the polyadenylation signal or the microRNA target regions, controlling the expression of the heterologous nucleotide sequence present in the recombinant baculovirus genome will ultimately depend on the host cell used for the expression of the product of said heterologous sequence. Should the host cell be an insect cell, promoters efficient in insect cells need to be used (for example, the p10 and polyhedrin very-late baculovirus promoters or a combination thereof). In case of a mammalian producer host cell, the promoter(s) may be mammalian promoters such as the human cytomegalovirus (CMV) promoter.

Cells according to the present invention can be selected from the group consisting of mammalian cells, preferably human cells, C. elegans cells, yeast cells, insect cells, and prokaryotic cells such as E. coli cells.

Preferred yeast cells for practicing the invention are S. cervisiae, S. pombe, C. albicans and P. pastoris.

Preferred E. coli cells for practicing the invention are Top10, DH5α, DH10β, TG1, BW23473, BW23474, MW003, and MW005 cells (Westernberg et al., 2010).

Preferred insect cells for practicing the invention are S. frugiperda cells, preferably Sf9, Sf21, Express Sf+ or Trichoplusia ni High Five cells, and D. melanogaster, preferably S2 Schneider cells.

Preferred human cells for practicing the invention are selected from the group consisting of HeLa, Huh7, HEK293, HepG2, KATO-III, IMR32, MT-2, pancreatic [beta]-cells, keratinocytes, bone-marrow fibroblasts, CHP212, primary neural cells, W12, SK-N-MC, Saos-2, W138, primary hepatocytes, FLC4, 143TK-, DLD-1, embryonic lung fibroblasts, primary foreskin fibroblasts, Saos-2 osteosarcoma, MRC5, and MG63 cells.

The invention will now be described in relation to the below examples and appended figures.

The AcMNPV bacmid has been inactivated for the chitinase, cathepsin, and p10 or p26, p10, p74 genes. The AAV rep2/cap8 expression cassette is inserted at the Tn7 site of the bacmid. On the same bacmid backbone, the rAAV gene (mSeAP in this example) is transferred at the Tn7 site.

FIG. 2. rAAV viral genome determination in bulk and purified samples.

rAAV productivity has been assessed in bulk samples or purified product samples originating from production performed with wt-; ΔCCΔp10-; ΔCCΔp26p10p74-baculovirus backbones.

rAAV titers are quantified through QPCR and expressed as viral genomes per mL (vg/mL)/mL (blue bars), contaminating baculovirus titers are quantified through QPCR in vg/ml (red dots). (a) rAAV bulk samples (b) immuno-affinity purified rAAV.

Figure 3A:
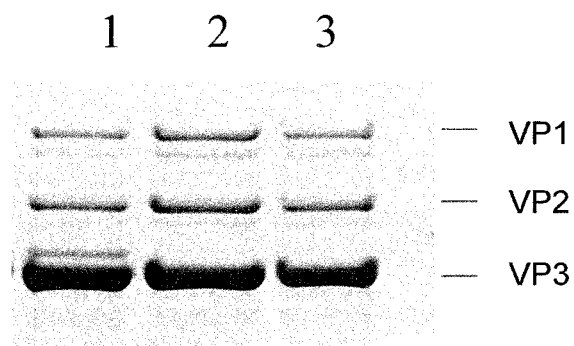
Figure 3B:
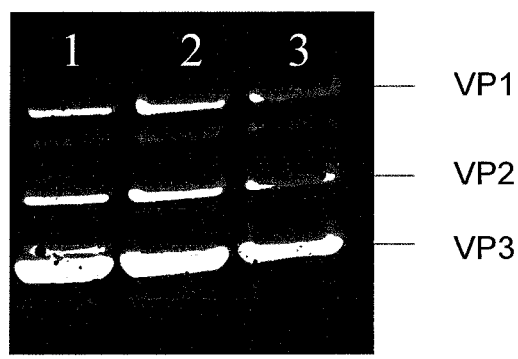

FIG. 3. Characterization of purified rAAV vectors.

Immuno-affinity purified rAAV vectors are analyzed through SDS-PAGE followed by Coomassie Blue staining (a) or Western blotting of the AAV VP proteins (b).

1: AAV-mSeAP ($5\times10^{10}$ vg) produced with baculovirus WT

2: AAV8-mSeAP ($5\times10^{10}$ vg) produced with baculovirus ΔCCΔp26p10p74

3: AAV8-mSeAP ($5\times10^{10}$ vg) produced with baculovirus ΔCCΔp10

FIG. 4. In vivo evaluation of rAAV vectors.

rAAV8-mSeAP produced either with WT or ΔCCΔp26p10p74 or ΔCCΔp10 baculoviruses was injected intramuscularly into mice at $10^9$ vg (n=4). (a) Time course expression of seric mSeAP is measured. (b) Histological analysis of mSeAP expression. Muscle sections (8 μM) were prepared and analyzed for mSeAP localization. (c) rAAV genome quantification in transduced muscle.

EXAMPLES

Materials and Methods

Baculovirus Gene Deletions

Deletion of cathepsin and chitinase from the wild type AcMNPV bacmid was performed from the E. coli DH10Bac strain containing the AcMNPV bacmid (Luckow et al., 1993) and transformed with plasmid pKD46 (Datsenko & Wanner, 2000). A PCR product necessary for the cathepsin/chitinase gene inactivation was generated with primers CC-KO-F and CC-KO-R (Table 1) using pCRTopo-loxCAT-lox as template (Marek et al., 2011). Gene inactivation was performed according to Marek et al., 2011 and assessed using primers chitinase-105625F and cathepsin-107849R (Table 1). CAT gene marker removal from cathepsin/chitinase null bacmid (AcbacΔCCΔcat) was performed as described (Marek et al., 2011) and was verified through PCR and sequencing, using the previously described primers. Second gene inactivation to remove the p10 coding sequence from AcbacΔCCΔcat was performed in the same manner, with a PCR product generated with primer pairs p10-KO-F/p10-KO-R (Table 1). Verification of the correct gene inactivation was performed using PCR and sequencing with primer pairs p10-118725-F/p10-119259-R (Table 1). This second gene inactivation led to cathepsin/chitinase/p10 null bacmid (AcbacΔCCΔp10), with an intact p10 promoter. Alternatively, the second gene inactivation of the neighboring genes p26-, p10, and p74 in AcbacΔCCΔcat was performed in a similar manner, with a PCR product generated with primer pairs p26-KO-F/p74-KO-R (Table 1). Verification of the correct gene inactivation was performed using PCR and sequencing with primer pairs p26-117989-F/p74-121176-R (Table 1). The latter gene inactivation led to cathepsin/chitinase/p26/p10/p74 null bacmid (AcbacΔCCΔp26p10p74).

Insertion of AAV Rep/Cap Genes and Recombinant AAV Genome into Bacmid by Transposition E. coli DH10Bac cells containing wild-type bacmid and E. coli DH10β cells containing AcbacΔCCΔp10 or AcbacΔCCΔp26p10p74 were transformed with plasmid pMON7124 (Luckow et al., 1993). Transposition was then performed according to the manual of the Bac-to-Bac system (Invitrogen) in to all these three bacmids with plasmid pFBD-mSeAP, encoding a murine secreted alkaline phosphatase reporter gene (mSeAP) controlled by a CMV promoter and flanked by Inverted Terminal Repeats (ITRs) of AAV2, Transposition was also performed with plasmid pSR660 encoding AAV2 rep78/52 gene under the polyhedrin very-late promoter and the AAV8 cap gene under the p10 very-late promoter (Smith et al., 2009) Efficient recombination into the bacmid genome was verified according to the Bac-to-Bac protocol. This resulted in three sets of two bacmids for the production of rAAV particles carrying ITR-mSeAP DNA, each set with a different baculoviral genomic backbone (wt, AcbacΔCCΔp10, or AcbacΔCCΔp26p10p74).

Cell Line, Baculovirus and rAAV Production

Sf9 cells in suspension culture were grown at 27° C. in SF900II medium (Invitrogen) in 1 L Bellco spinner flasks. Baculoviruses were generated according to the guidelines of the Bac-to-Bac protocol from the deleted bacmids and the recombinant bacmids described above and were amplified in suspension cultures of Sf9 cells in 100 mL Bellco spinners. rAAV production was performed by dual infection of Sf9 cells with baculoviruses harboring the recombinant AAV genome (ITR-mSeAP) and AAV rep2/cap8 genes, each at an MOI of 1.6 in 70 mL of Sf9 cell culture seeded at $10^6$ cells/mL in 100 mL Bellco spinners. At 72 h post-infection, 1 mL of the total culture was recovered for direct quantification of rAAV production prior to purification and then stored at –80° C.

rAAV Purification and Characterization rAAV was purified from bulk on Immuno-affinity AVB sepharose medium (GE Healthcare) accordingly to (Smith et al., 2009). $5 \times 10^{10}$ viral genome (vg) of purified rAAV vectors were run on SDS-PAGE Bis-Tris 4-12% (Nu-PAGE, Invitrogen), and either directly coomassie stained or transferred to Nitrocellulose membrane (iBlot gel transfer stack nitrocellulose, Invitrogen) prior to immuno detection (see below Western blotting).

Determination of rAAV Genome Titer

A quantitative PCR assay was performed directly on the total culture samples or purified rAAV samples to determine rAAV titer (viral genome per mL of production). Viral DNA was extracted directly from bulk or purified samples using MagNA Pure DNA and viral RNA small volume kit (MagNA Pure 96, Roche). The plasmid used as reference contains the two ITRs of AAV2 and the baculovirus DNA polymerase gene. Serial dilutions were performed to calculate the final copy number of the analyzed sample and a positive control was used to assess efficient titration. Titrations were performed at the same time on the same plate by an independent operator.

Western Blot

Baculovirus bulk samples or purified rAAV8 samples were analyzed through Western blot for AAV VP and Rep proteins.

Anti VP primary antibody is a mouse IgG1 clone B1 (Progen) used in a $1/250^{th}$ dilution. Anti Rep primary antibody is a mouse IgG1 clone 303.9 (Progen) used in a $1/100^{th}$ dilution. Secondary antibody is a goat anti-mouse Dye 680 (LI-COR) used in a $1/5000^{th}$ dilution. Incubation was performed in infrared imaging system blocking buffer (LI-COR) and revelation was performed on the Odyssey system (LI-COR). Intensities of fluorescence were quantified with Odyssey 2.1 software.

In Vivo Injection, Sample Collection and mSeAP Quantification rAAV vectors, $10^9$ vg in 25 μL of phosphate buffered saline, were injected intra-muscularly into the left Tibialis Anterior (TA) muscle of C57black6 mice, 6 weeks old (n=4 per vector). Blood samples were collected from injected mice at 3, 7, 14, 21, 28, 35 days post-injection, for mSeAP seric quantification. At day 35, the animals were sacrificed and TA muscles, left and right were collected and frozen before histological and enzymatic assays.

All mice were handled according to directive 2010/63/EU on the protection of animals used for scientific purposes. A mSeAP dosage assay was performed with 12.5 μL of mouse serum. mSeAP quantification was realised using the Phospha-Light System kit (Applied Biosystems). Samples were read on a Victor II Luminometer apparatus. Expression levels are expressed as ng of mSeAP per ml, of serum using a standard curve of purified human placental alkaline phosphatase (Applied Biosystems).

Histological Analysis of mSeAP Expression

Muscle sections (8 μM) were prepared and analyzed for mSeAP localization using the Nitro Blue Tetrazolium/5-Bromo-4-Chloro-3-Indolyl-Phosphate method, as described before (Riviere et al., 2006). Muscle sections were counter-stained with nuclear fast red, and inflammation and muscle integrity were evaluated by hematoxylin-eosin staining and light microscopy analysis.

Detection of rAAV Genome In Vivo

Total DNA samples were extracted from mouse muscle using FastDNA kit (QBIOgene) on a FastPrep apparatus (QBIOgene). rAAV genome titration was performed using QPCR as described in previous section. Normalization was performed using quantification of the titin gene.

Statistical Analysis

Statistical significance of seric mSeAP expression at 35 days following rAAV injection was evaluated. Group comparisons were performed. Variance analysis were performed through Fischer test ($\alpha$=0.05), followed by Student test ($\alpha$=0.05) using Excel program.

Results:

Generation of Baculoviruses Deleted for the Chitinase, Cathepsin, Together with the p10 or the p26, p10, and p74 Genes.

In order to remove multiple genes, sequential deletions need to be introduced in the AcMNPV bacmid. A well-known and established method to investigate gene functions is the manipulation of a baculovirus genome in bacteria by homologous recombination using ET (E. coli. RecE & RecT proteins) or lambda red based recombination directed at a single gene, which is then replaced by an antibiotic selection marker (Datsenko & Wanner, 2000). In order to prepare multiple deletions within the same genome, several different selection markers need to be used or the selection marker needs to be flanked by unique restriction sites, allowing removal after each gene deletion, by digestion and re-ligation. A strategy derived from a method to make deletions/insertions in a bacterial genome (Suzuki et al., 2007; Suzuki et al., 2005) has been adapted for bacmid technology (Marek et al., 2011). After replacement of the first gene with the chloramphenicol acetyl transferase antibiotic marker by homologous recombination, the marker can be removed due to the presence of loxP sites at both ends of the marker. In the setup used, two modified loxP sites are used (lox66 and lox71), each with a different mutation. After recombination by cre-recombinase a lox72 site is left (Lambert et al., 2007), which has now two mutations instead of one, and can no longer be recognized by the cre-recombinase. This allows the subsequent deletion of a second target gene. This method was tested in a bacmid set up to serially remove in two steps the chi/v-cath (deleted nucleotides 105282-107954 according to AcMNPV genetic map (Ayres et al., 1994)) and p10 (deleted nucleotides 118839-119121) or p26/p10/p74 (deleted nucleotides 118044-121072) genes. These deletions were assessed by PCR and sequencing. Sf9 cells were transfected successfully with each of the deletion bacmid DNAs. 96 h post-infection visible signs of baculovirus infection (disruption of the cell layers, higher Sf9 cells diameter and mortality) were observed indicating infectivity of both the AcΔCCΔp10 and AcΔCCΔp26p10p74 baculoviruses.

Figure 1:
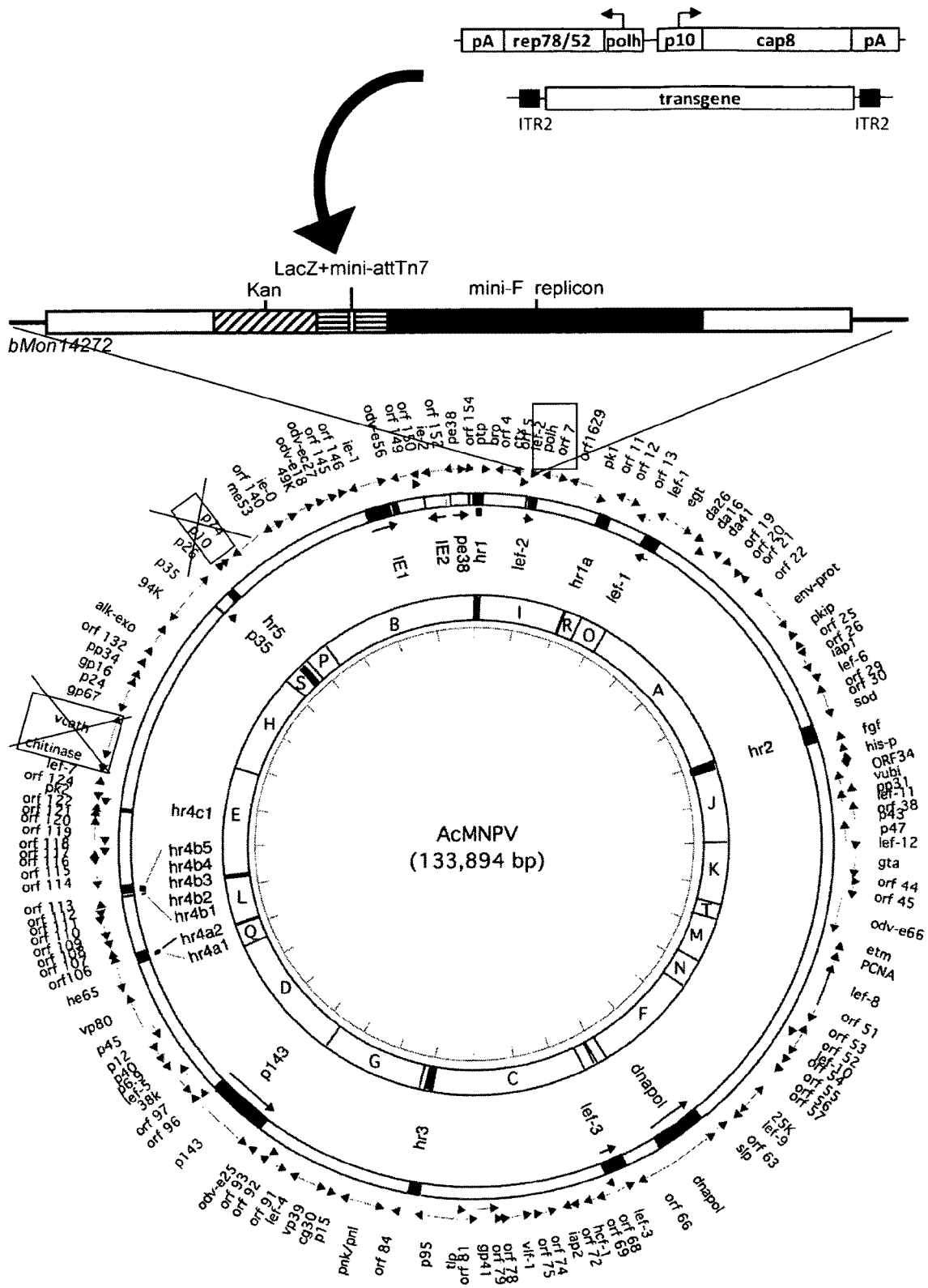
FIG. 1. Schematic map of the AcMNPV bacmid deleted of chitinase, cathepsin, and the p10 ORF, leaving the p10 promoter intact (ΔCCΔp10) or in combination with a deletion of the p26, p10, and p74 genes (ΔCCΔp26p10p74).

Prior to transposition of AAV2 rep gene under the polh and AAV8 cap gene under p10 promoter and AAV-mSeAP sequences in AcΔCCΔp10, *E. coli* DH10β cells, containing the different bacmid constructs, were transformed with plasmid pMON7124 (Luckow et al., 1993) to mediate efficient recombination from transfer vectors containing the constructs of interest into the Tn7 site of the bacmid (FIG. 1).

Following recombination, and prior to bacmid DNA transfection into the Sf9 cells, the absence of non-recombinant bacmid was verified.

The baculoviruses were plaque purified and amplified for two passages. No difference was observed in terms of baculovirus titers (pfu/ml) or AAV VP and Rep protein levels between the recombinant wt-, ΔCCΔp10, and ΔCCΔp26p10p74 baculoviruses. The baculoviruses were then used to perform rAAV production.

the Deletion of Chitinase, Cathepsin and p10 Genes does not Improve rAAV Productivity in Sf9 Cells.

Figure 2A:
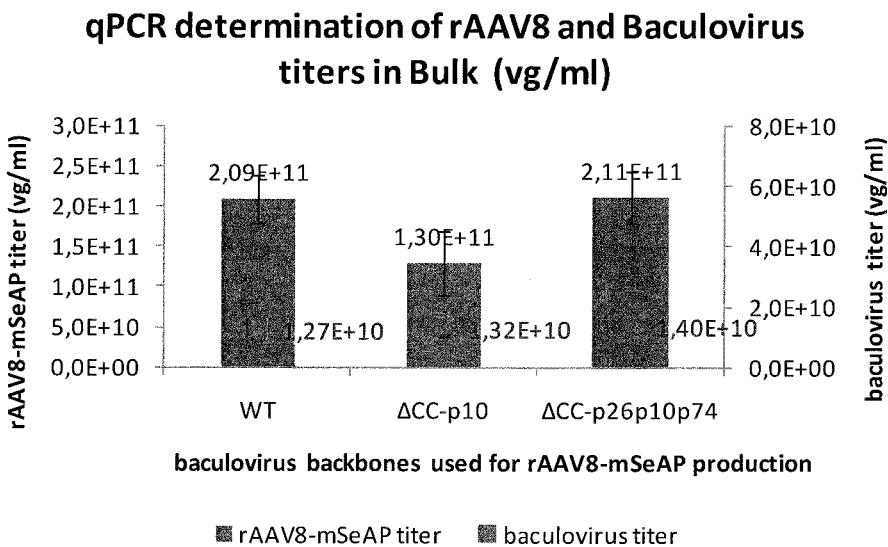
Figure 2B:
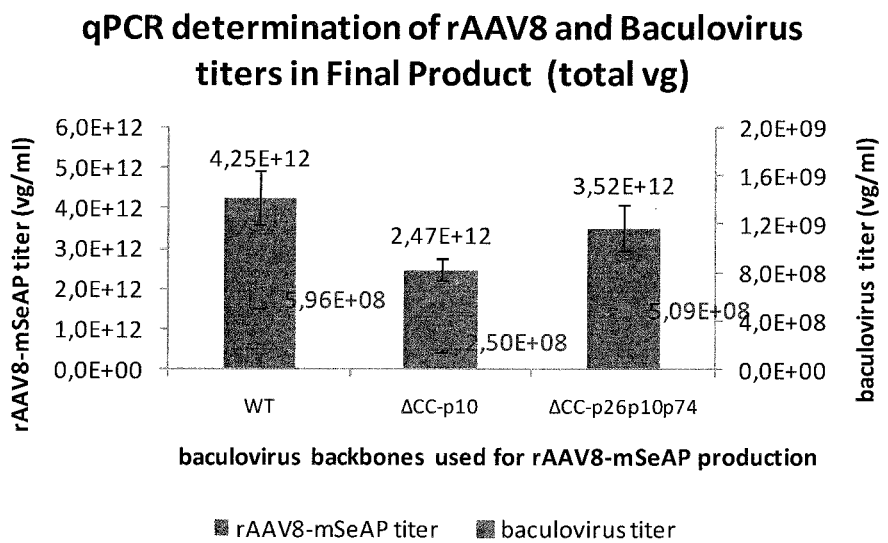

Standard rAAV vector productions were performed in spinner cultures clearly showing that the production of recombinant baculovirus, either of the wild-type or the ΔCCΔp10-type or the ΔCCΔp26p10p74-type, was comparable leading to titers of $2.09 \times 10^{11}$ and $1.30 \times 10^{11}$ and $2.11 \times 10^{11}$ vg/mL, respectively. Equally, the production of AAV (model transgene: mSeAP) was practically similar when both baculoviruses are used, leading to titers of $1.27 \times 10^{10}$, $1.32 \times 10^{10}$ and $1.40 \times 10^{10}$ vg/mL, respectively (FIG. 2A). The purification of AAV using AVB chromatography led to increases in titer to $4.25 \times 10^{12}$ and $2.47 \times 10^{12}$, $3.52 \times 10^{12}$ vg/mL, respectively (FIG. 2B).

These results indicate that the removal of some non-essential baculovirus genes from the baculovirus backbone has no impact on the production and purification of AAV vectors.

the Use of a Baculovirus Deleted of Chitinase, Cathepsin and p10 or p26, p10, p74 Genes Reduces rAAV Particle Degradation.

The absence of the chitinase, cathepsin, in combination with a p10 ORF deletion or a deletion of the p26, p10 and p74 genes had a beneficial effect on AAV-vector integrity. Most likely, the absence of protease activity (cathepsin) derived from the baculovirus led to reduced vector particle degradation as shown by SDS-PAGE and Western blot (WB) analysis (FIG. 3). These analytical methods clearly indicated the disappearance of at least three VP-specific 'contaminating degradation bands'. The major contaminating degradation band of the three bands is localized closed to VP3 (FIG. 3). The use of ΔCCΔp10 or ΔCCΔp26p10p74 baculoviruses instead of wt-baculoviruses thus leads to reduced rAAV vector degradation and to the disappearance of several VP degradation products.

rAAV Particles Produced Using a Baculovirus Deleted of Chitinase, Cathepsin and p10 or p26, p10, p74 Genes Display Higher Infectivity In Vivo.

Figure 4A:
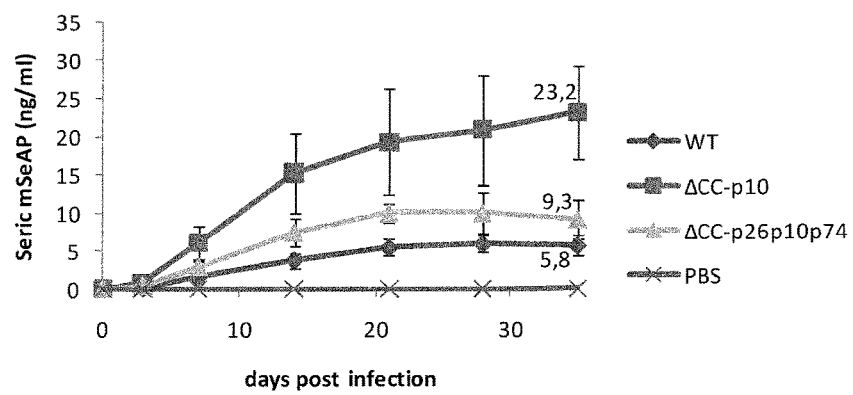

The disappearance of certain sub-sized protein bands in the WB when using the ΔCCΔp10 or ΔCCΔp26p10p74 baculoviruses signifies that the rAAV vector particle is less degraded and may have a better integrity, suggesting that the in vivo infectivity/potency may be improved. In fact when injecting purified rAAV-mSeAP particles produced with the three different baculovirus backbones (wt, ΔCCΔp10 and ΔCCΔp26p10p74) intra-muscularly into mice (C57Black6), mSeAP activity was observed in the serum about 1 week after injection. The activity increased to plateau levels of about 5.8 ng/mL, 23.2 ng/mL, and 9.3 ng/mL when using the wt-backbone, ΔCCΔp10- and ΔCCΔp26p10p74-backbones for AAV production, respectively, at 3 weeks post-injection (FIG. 4A). The difference is in the order of a factor 4 when using the ΔCCΔp10-baculovirus backbone for rAAV production, compared to wt-baculovirus backbone (p=0.01). The difference is in the order of a factor 2 when using ΔCCΔp26p10p74-backbone in place of the wt-backbone (p=0.05).

Figure 4B:
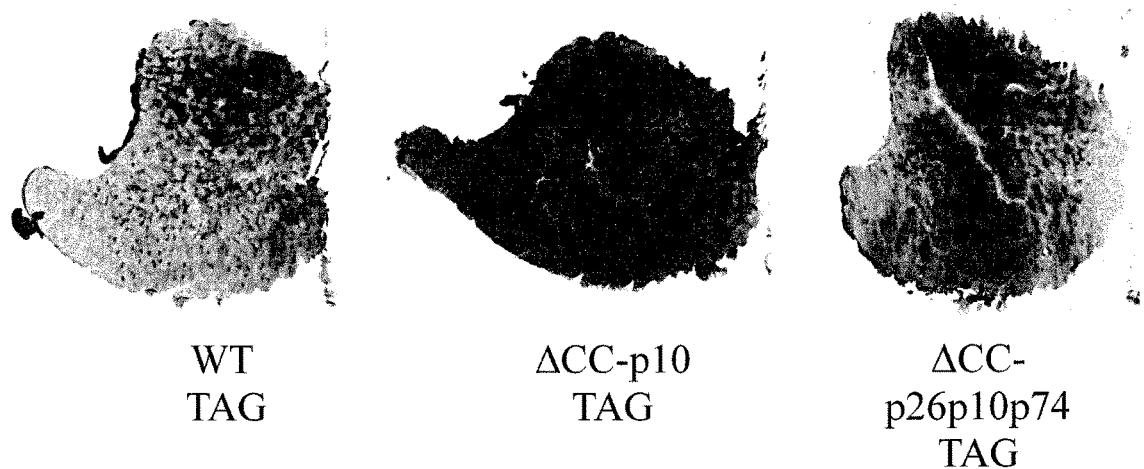
Figure 4C:
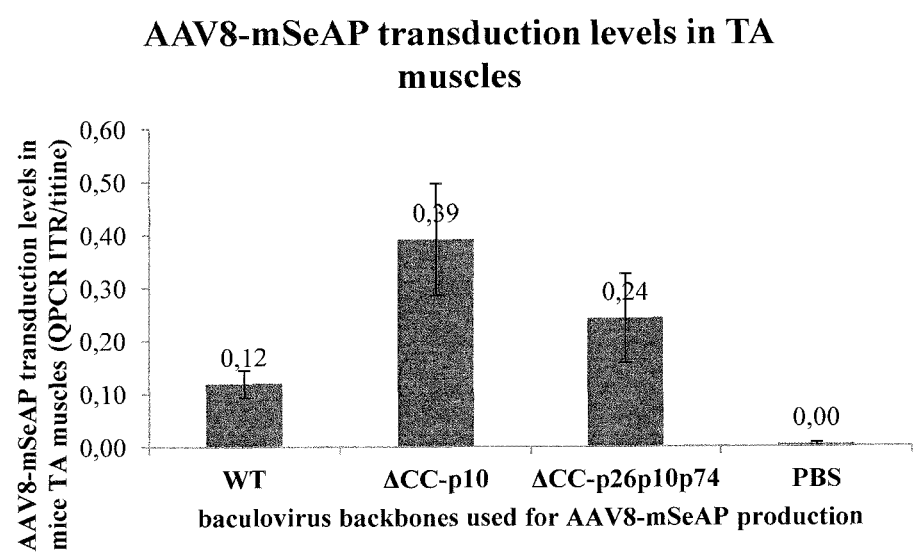

Thirty-five days after injection, the mice were sacrificed and the injected muscles were histologically analyzed. As for the increased serum levels of mSeAP activity, the mice injected with rAAV produced with the ΔCCΔp10 baculovirus showed a considerably increased mSeAP activity in the transduced muscle tissue in comparison to those mice injected with rAAV produced with the wt-baculovirus system. The mSeAP activity in the muscle tissue transduced with rAAV produced with ΔCCΔp26p10p74 was found in the middle range compared to the rAAV produced with the two other baculovirus backbones (FIG. 4B). The increased mSeAP activity observed with rAAV produced with the ΔCCΔp10 baculovirus is correlated with an increase in rAAV genome copy number delivered to the TA muscle cells as shown by quantitative PCR (FIG. 4C), illustrating that 3.25 more genome copies were delivered compared to the wt production system. In a similar manner, evaluation of the rAAV genome copy number delivered to the TA muscle cells following production with ΔCCΔp26p10p74 baculovirus led to a 2 fold increase compared to the use of rAAV produced with wt-baculovirus backbone (FIG. 4C). These values are in good accordance with the mSeAP activity levels obtained with the various baculovirus vectors.

REFERENCES

Ayres M D, Howard S C, Kuzio J, Lopez-Ferber M, Possee R D (1994). The complete DNA sequence of *Autographa californica* nuclear polyhedrosis virus. Virology 202(2): 586-605.

Carbonell L F, Hodge M R, Tomalski M D, Miller L K (1988). Synthesis of a gene coding for an insect-specific scorpion neurotoxin and attempts to express it using baculovirus vectors. Gene 73, 409-18.

Datsenko K A, Wanner B L (2000). One-step inactivation of chromosomal genes in *Escherichia coli* K-12 using PCR products. PNAS 97(12): 6640-6645.

Friesen P D & Miller L K (1986). The regulation of baculovirus gene expression in: "The Molecular Biology of Baculoviruses" (W. Doerfler and P. Boehm, eds.) Springer-Verlag, Berlin, pp. 31-49.

Hitchman R B, Possee R D, Crombie A T, Chambers A, Ho K, Siaterli E, Lissina O, Sternard H, Novy R, Loomis K, Bird L E, Owens R J, King L A (Epub 2009 Aug. 5) Genetic modification of a baculovirus vector for increased expression in insect cells. Cell Biol Toxicol.

Kaba S A, Salcedo A M, Wafula P O, Vlak J M, van Oers M M (2004). Development of a chitinase and v-cathepsin negative bacmid for improved integrity of secreted recombinant proteins. J Virol Methods 122(1): 113-118.

Lambert J M, Bongers R S, Kleerebezem M (2007). Cre-lox-Based System for Multiple Gene Deletions and Selectable-Marker Removal in *Lactobacillus plantarum*. Appl Environ Microbiol 73(4): 1126-1135.

Lebacq-Verheyden A M, Kasprzyk P G, Raum M G, Van Wyke Coelingh K, Lebacq J A, Battey J F. (1988).

Posttranslational processing of endogenous and of baculovirus-expressed human gastrin-releasing peptide precursor. Molecular and Cell Biology 8, 3129-35.

Luckow V A, Summers M D (1988). Trends in the development of baculovirus expression vectors. Bio Technology 6, 47-55.

Luckow V A, Lee S C, Barry G F, Olins P O (1993). Efficient generation of infectious recombinant baculoviruses by site-specific transposon-mediated insertion of foreign genes into a baculovirus genome propagated in *Escherichia coli*. J Virol 67(8): 4566-4579.

Lynn D E (2007). Available lepidopteran insect cell lines. In Methods Mol Biol, pp. 117-137.

Maeda S, Kawai T, Obinata M, Fujiwara H, Horiuchi T, Saeki Y, Sato Y, Furusawa M. (1985). Production of human alpha-interferon in silkworm using a baculovirus vector. Nature 315, 592-4.

Manno C S, Pierce G F, Arruda V R, Glader B, Ragni M et al. (2006). Successful transduction of liver in hemophilia by AAV-Factor IX and limitations imposed by the host immune response. Nat Med 12(3): 342-347.

Marek M, van Oers M M, Devaraj F F, Vlak J M, Merten O W (2011). Engineering of baculovirus vectors for the manufacture of virion-free biopharmaceuticals. Biotechnol Bioeng 108(5): 1056-1067.

Martin B M, Tsuji S, LaMarca M E, Maysak K, Eliason W, Ginns E I (1988). Glycosylation and processing of high levels of active human glucocerebrosidase in invertebrate cells using a baculovirus expression vector. DNA 7, 99-106.

McKenna K A, Hong H, van Nunen, Granados R R (1989). Establishment of new *Trichoplusia ni* cell lines in serum-free medium for baculovirus and recombinant protein production. Journal of Invertebrate Pathology 71, 82-90.

Mendell J R, Rodino-Klapac L R, Rosales X Q, Coley B D, Galloway G et al. (2010). Sustained alpha-sarcoglycan gene expression after gene transfer in limb-girdle muscular dystrophy, type 2D. Ann Neurol 68(5): 629-638.

Miller D W, Safer P, Miller L K (1986). in Genetic Engineering: Principles and Methods Vol. 8 (eds Setlow, J. & Hollaender, A.) Plenum Publishing, New York, pp. 277-298.

Miller L K (1988). Baculoviruses as gene expression vectors. Annual Review Microbiology. 42, 177-99.

Miyajima A, Schreurs J, Otsu K, Kondo A, Arai K, Maeda S (1987). Use of the silkworm, *Bombyx mori*, and an insect baculovirus vector for high-level expression and secretion of biologically active mouse interleukin-3 Gene 58, 273-81.

Simonelli F, Maguire A M, Testa F, Pierce E A, Mingozzi F et al. (2010). Gene Therapy for Leber's Congenital Amaurosis is Safe and Effective Through 1.5 Years After Vector Administration. Mol Ther 18(3): 643.

Smith G E, Ju G, Ericson B L, Moschera J, Lahm H W, Chizzonite R, Summers M D (1985). Modification and secretion of human interleukin 2 produced in insect cells by a baculovirus expression vector. Proceedings National Academy of Sciences USA 82, 8404-8.

Smith G E, M D Summers (1979). Restriction maps of five *Autographa californica* nuclear polyhedrosis virus (MNPV) variants, *Trichoplusia ni* MNPV and *Galleria mellonella* MNPV DNAs with endonucleases SmaI, KpnI, BamHI, SacI, XhoI, and EcoRI. J. Viol. 30:828-838.

Smith R H, Levy J R, Kotin R M (2009). A Simplified Baculovirus-AAV Expression Vector System Coupled With One-step Affinity Purification Yields High-titer rAAV Stocks From Insect Cells. Mol Ther 17(11): 1888-1896.

Suzuki N, Nonaka H, Tsuge Y, Inui M, Yukawa H (2005). New multiple-deletion method for the *Corynebacterium glutamicum* genome, using a mutant lox sequence. Appl Environ Microbiol 71(12): 8472-8480.

Suzuki N, Inui M, Yukawa H (2007). Site-directed integration system using a combination of mutant lox sites for *Corynebacterium glutamicum*. Appl Microbiol Biotechnol 77(4): 871-878.

Van Oers M M (2011). Opportunities and challenges of the baculovirus expression system. Journal of Invertebrate Pathology (in press).

Vlak J M, Klinkenberg F A, Zaal K J, Usmany M, Klinge-Roode E C, Geervliet J B, Roosien J, van Lent J W (1988). Functional studies on the p10 gene of *Autographa californica* nuclear polyhedrosis virus using a recombinant expressing a p10-beta-galactosidase fusion gene. *Journal of General Virology* 69, 765-76.

Westenberg M, Bamps S, Soedling H, Hope I A, Dolphin C T (2010). *Escherichia coli* MW005: Lambda Red-mediated recombineering and copy-number induction of oriV-equipped constructs in a single host. BMC Biotechnol 10.

SEQUENCE LISTING

TABLE 1

Primer sequences used in this study

| Primer | Sequence 5' to 3' | Purpose* |
|---|---|---|
| CC-KO-F | CCGCTGTTGAAACAATATTTTATAATACCCTGTTTATAGTTAACAAT GTCGGCAGCGTCTATGGCCATAGGAATAGGGCCTACCGTTCGTATAA TGTATGCTATACGAAGTTAT (SEQ ID NO: 1) | chitinase/cathepsin gene inactivation nt 105771-107700 |
| CC-KO-R | CCGCTGTTGAAACAATATTTTATAATACCCTGTTTATAGTTAACAAT GTCGGCAGCGTCTATGGCCATAGGAATAGGGCCTACCGTTCGTATAA TGTATGCTATACGAAGTTAT (SEQ ID NO: 2) | |
| chitinase-105625F | CGCGGCCGTACATGGCGACGCCCA (SEQ ID NO: 3) | Verification |
| cathepsin-107849R | GTTTTTAAAGGTCCAATATGGAATG (SEQ ID NO: 4) | Verification |
| p10-KO-F | TTGTATATTAATTAAAATACTATACTGTAAATTACATTTTATTTAC AATCTACCGTTCGTATAGCATACATTATACGAAGTTAT (SEQ ID NO: 5) | p10 coding sequence inactivation (start codon to stop codon) nt 118839-119121 |

TABLE 1-continued

Primer sequences used in this study

| Primer | Sequence 5' to 3' | Purpose* |
|---|---|---|
| P10-KO-R | GAATCGTACGAATATTATAAAACAATTGATTTGTTATTTTAAAAA CGATTTACCGTTCGTATAATGTATGCTATACGAAGTTAT (SEQ ID NO: 6) | |
| p10-118725-F | CCGGGACCTTTAATTCAACCCAACA (SEQ ID NO: 7) | Verification |
| p10-119259-R | CAGCATTTGTTATACACACAGAACT (SEQ ID NO: 8) | Verification |
| M13 PUC F | CCAGTCACGACGTTGTAAAACG (SEQ ID NO: 9) | Verification of transposed bacmids |
| M13 PUC R | AGCGGATAACAATTTCACACAGG (SEQ ID NO: 10) | Verification of transposed bacmids |
| Genta | AGCCACCTACTCCCAACATC (SEQ ID NO: 11) | Verification of transposed bacmids |

*Baculovirus numbering is according to Ayres et al., 1994

The invention claimed is:

1. A method for producing a recombinant adeno-associated virus (rAAV) vector, comprising infecting a cell with one or several recombinant baculovirus(es), each baculovirus comprising a recombinant baculovirus genome harboring a heterologous sequence;
wherein the heterologous sequence from each of the one or several recombinant baculovirus(es) encodes a different part of said rAAV vector; and
wherein each of the one or several recombinant baculovirus(es) comprises a recombinant baculovirus genome comprising the p26 and p74 baculoviral genes, and wherein the baculoviral genes cathepsin, chitinase and p10 are disrupted in each of the one or several recombinant baculovirus(es).

2. The method according to claim 1, wherein the one or several recombinant baculovirus(es) encode a recombinant AAV genome, recombinant Rep protein and recombinant Cap protein.

3. The method according to claim 1, wherein the p10 gene is disrupted without deleting the p10 promoter.

4. The method according to claim 1, wherein the cell is an insect cell.

5. The method according to claim 1, wherein the genome(s) of the one or several baculovirus(es) is derived from *Autographa californica* nuclear polyhedrosis virus (AcMNPV).

6. The method according to claim 1, comprising infecting the cell with three baculoviruses:
(i) a baculovirus encoding the AAV Rep protein,
(ii) a baculovirus encoding the AAV Cap protein; and
(iii) a baculovirus encoding the AAV-Inverted Terminal Repeats (AAV-ITRs) genome comprising a gene of interest between the two AAV-ITRs.

7. The method according to claim 1, comprising infecting the cell with two baculoviruses:
(i) a baculovirus encoding the AAV Rep protein and the AAV Cap protein; and
(ii) a baculovirus encoding the AAV-ITR genome comprising a gene of interest between the two AAV-ITRs.

8. A method for producing an rAAV vector, comprising infecting an insect cell with three recombinant baculoviruses:
(i) a baculovirus encoding the AAV Rep protein,
(ii) a baculovirus encoding the AAV Cap protein; and
(iii) a baculovirus encoding the AAV-ITR genome comprising a gene of interest between the two AAV-ITRs;
wherein each of the recombinant baculoviruses comprises a recombinant baculovirus genome derived from the AcMNPV genome comprising the p26 and p74 baculoviral genes,
wherein the baculoviral genes cathepsin, chitinase and p10 are disrupted in each of the recombinant baculoviruses, and
wherein the p10 gene is disrupted without deleting the p10 promoter.

9. A method for producing an rAAV vector, comprising the step of infecting an insect cell with two recombinant baculoviruses:
(i) a baculovirus encoding the AAV Rep protein and the AAV Cap protein; and
(ii) a baculovirus encoding the AAV-ITR genome comprising a gene of interest between the two AAV-ITRs;
wherein each of the recombinant baculoviruses comprises a recombinant baculovirus genome derived from the AcMNPV genome comprising the p26 and p74 baculoviral genes,
wherein the baculoviral genes cathepsin, chitinase and p10 are disrupted in each of the recombinant baculoviruses, and
wherein the p10 gene is disrupted without deleting the p10 promoter.

* * * * *

UNITED STATES PATENT AND TRADEMARK OFFICE
CERTIFICATE OF CORRECTION

Page 1 of 1

PATENT NO. : 10,480,010 B2
APPLICATION NO. : 14/234949
DATED : November 19, 2019
INVENTOR(S) : Lionel Galibert et al.

It is certified that error appears in the above-identified patent and that said Letters Patent is hereby corrected as shown below:

In the Specification

Column 3,
Line 29, "Westerberg" should read --Westernberg--.

Column 9,
Line 40, "the Use" should read --The use--.

Signed and Sealed this
Twenty-third Day of June, 2020

Andrei Iancu
*Director of the United States Patent and Trademark Office*

SEQUENCE LISTING

<160> NUMBER OF SEQ ID NOS: 11

<210> SEQ ID NO 1
<211> LENGTH: 114
<212> TYPE: DNA
<213> ORGANISM: artificial
<220> FEATURE:
<223> OTHER INFORMATION: primer

<400> SEQUENCE: 1
ccgctgttga aacaatattt tataataccc tgtttatagt taacaatgtc ggcagcgtct    60
atggccatag gaatagggcc taccgttcgt ataatgtatg ctatacgaag ttat          114

<210> SEQ ID NO 2
<211> LENGTH: 114
<212> TYPE: DNA
<213> ORGANISM: artificial
<220> FEATURE:
<223> OTHER INFORMATION: primer

<400> SEQUENCE: 2
ccgctgttga aacaatattt tataataccc tgtttatagt taacaatgtc ggcagcgtct    60
atggccatag gaatagggcc taccgttcgt ataatgtatg ctatacgaag ttat          114

<210> SEQ ID NO 3
<211> LENGTH: 24
<212> TYPE: DNA
<213> ORGANISM: artificial
<220> FEATURE:
<223> OTHER INFORMATION: primer

<400> SEQUENCE: 3
cgcggccgta catggcgacg ccca                                           24

<210> SEQ ID NO 4
<211> LENGTH: 25
<212> TYPE: DNA
<213> ORGANISM: artificial
<220> FEATURE:
<223> OTHER INFORMATION: primer

<400> SEQUENCE: 4

-continued gtttttaaag gtccaatatg gaatg                                         25

<210> SEQ ID NO 5
<211> LENGTH: 84
<212> TYPE: DNA
<213> ORGANISM: artificial
<220> FEATURE:
<223> OTHER INFORMATION: primer

<400> SEQUENCE: 5
ttgtatatta attaaaatac tatactgtaa attacatttt atttacaatc taccgttcgt    60
atagcataca ttatacgaag ttat                                          84

<210> SEQ ID NO 6
<211> LENGTH: 84
<212> TYPE: DNA
<213> ORGANISM: artificial
<220> FEATURE:
<223> OTHER INFORMATION: primer

<400> SEQUENCE: 6
gaatcgtacg aatattataa aacaattgat ttgttatttt aaaaacgatt taccgttcgt    60
ataatgtatg ctatacgaag ttat                                          84

<210> SEQ ID NO 7
<211> LENGTH: 25
<212> TYPE: DNA
<213> ORGANISM: artificial
<220> FEATURE:
<223> OTHER INFORMATION: primer

<400> SEQUENCE: 7
ccgggacctt taattcaacc caaca                                         25

<210> SEQ ID NO 8
<211> LENGTH: 25
<212> TYPE: DNA
<213> ORGANISM: artificial
<220> FEATURE:
<223> OTHER INFORMATION: primer

<400> SEQUENCE: 8
cagcatttgt tatacacaca gaact                                         25

<210> SEQ ID NO 9
<211> LENGTH: 22
<212> TYPE: DNA
<213> ORGANISM: artificial
<220> FEATURE:
<223> OTHER INFORMATION: primer

<400> SEQUENCE: 9
ccagtcacga cgttgtaaaa cg                                            22

<210> SEQ ID NO 10
<211> LENGTH: 23
<212> TYPE: DNA
<213> ORGANISM: artificial
<220> FEATURE:
<223> OTHER INFORMATION: primer

<400> SEQUENCE: 10
agcggataac aatttcacac agg                                           23

-continued

```
<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11
agccacctac tcccaacatc                                                20
```